United States Patent
Billeb et al.

Patent Number: 5,349,104
Date of Patent: Sep. 20, 1994

[54] STABILIZED AMINOBENZOTRIFLUORIDES

[75] Inventors: Gilbert Billeb; Günther Semler, both of Kelkheim/Ts, Fed. Rep. of Germany

[73] Assignee: Hoechst Aktiengesellschaft, Frankfurt am Main, Fed. Rep. of Germany

[21] Appl. No.: 58,281

[22] Filed: May 4, 1993

[30] Foreign Application Priority Data

May 5, 1992 [DE] Fed. Rep. of Germany ....... 4214849

[51] Int. Cl.$^5$ ............................................. C07C 209/82
[52] U.S. Cl. ............................................. 564/5; 564/6; 564/307; 564/309; 564/441; 564/442
[58] Field of Search .................. 564/5, 6, 307, 309, 564/441, 442

[56] References Cited

U.S. PATENT DOCUMENTS

| | | | |
|---|---|---|---|
| 2,681,935 | 6/1954 | Thompson | 564/5 |
| 2,911,340 | 11/1959 | Franklin et al. | 564/5 X |
| 2,913,495 | 11/1959 | Goldsmith | 564/5 |
| 3,324,011 | 6/1967 | Baum et al. | 203/6 |
| 4,990,663 | 2/1991 | Chang et al. | 564/5 |

FOREIGN PATENT DOCUMENTS

1121058 1/1962 Fed. Rep. of Germany.
3287566 12/1991 Japan.

OTHER PUBLICATIONS

Jones, R. G., *J. Amer. Chem. Soc.* 69:2346–2350 (1947).

*Primary Examiner*—Richard L. Raymond
*Attorney, Agent, or Firm*—Connolly & Hutz

[57] ABSTRACT

Without added stabilizers, aminobenzotrifluorides have low thermal and storage stability.

The present invention relates to preparations of a stabilized amionbenzotrifluoride, composed essentially of
a) an aminobenzotrifluoride of the formula (I),

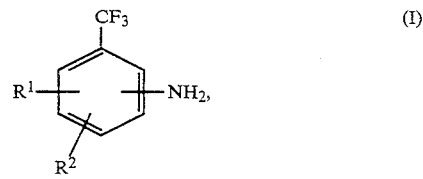

in which
$R^1$ and $R^2$, independently of each other, are hydrogen, $C_1$–$C_6$-alkyl, $C_2$–$C_6$-alkenyl, substituted or unsubstituted aryl, halogen, $CF_3$, nitro, amino, methoxy, hydroxyl or $NR^3R^4$, where $R^3$ and $R^4$, independently of each other, are hydrogen or $C_1$–$C_5$-alkyl radicals, and the $NH_2$ group can be located in the 2-, 3- or 4-position in relation to the $CF_3$ group, and
b) at least one base.

15 Claims, No Drawings

STABILIZED AMINOBENZOTRIFLUORIDES

Aminobenzotrifluorides are of great industrial importance as starting materials for the preparation of numerous relevant compounds, for example in the fields of plant protective agents and pharmaceuticals.

Aminobenzotrifluorides have low thermal and storage stability. R. G. Jones, J. Amer. Chem. Soc. 69, 2346 (1947) reported that 2- and 4-aminobenzotrifluorides change into glass-like polymers on heating.

2-Aminobenzotrifluoride resinifies at 140° to 150° C. in less than 2 hours. 4-Aminobenzotrifluoride is no longer stable even at 120° C., and resinifies within 1.5 hours. While chlorine substituents on the ring do increase the stability, even in this case resinification sets in at about 180° C. This property impedes the purification of these compounds, for example by distillation, substantially, since the boiling points, even under reduced pressure, are very close to the decomposition temperature. The distillates are often more unstable than the crude products. In the case of the storage of these compounds, too, for example as melts, precautions must be taken against overheating, especially since resinification takes place exothermically.

The object on which the present invention was based was therefore to make available aminobenzotrifluorides in a stabilized form, in which they no longer suffer from the disadvantages described above.

It has been found, surprisingly, that aminobenzotrifluorides can be stabilized against thermal decomposition and resinification if a basic compound is added to them.

The present invention relates to preparations of a stabilized aminobenzotrifluoride, composed essentially of a) an aminobenzotrifluoride of the formula (I),

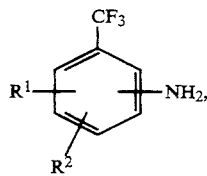

in which $R^1$ and $R^2$, independently of each other, are hydrogen, $C_1$–$C_6$-alkyl, preferably $C_1$–$C_4$-alkyl, in particular methyl; $C_2$–$C_6$-alkenyl, preferably $C_2$–$C_4$-alkenyl; substituted or unsubstituted aryl, preferably unsubstituted or substituted phenyl, in particular phenyl, hydroxyphenyl, tolyl, xylyl, aminophenyl, halophenyl and nitrophenyl; halogen, preferably fluorine, chlorine or bromine; $CF_3$, nitro, amino, methoxy, hydroxyl or —$NR^3R^4$, where $R^3$ and $R^4$, independently of each other, are hydrogen or $C_1$–$C_5$-alkyl radicals, preferably hydrogen or $C_1$–$C_3$-alkyl radicals, and the $NH_2$ group can be located in the 2-, 3- or 4-position in relation to the $CF_3$ group, and b) at least one base.

Bases which are preferably employed according to the invention are primary, secondary or tertiary aliphatic or araliphatic amines of the formulae (IIa) or (IIb) or cycloaliphatic amines of the formula (IIc)

$$R^5R^6R^7N, \quad \text{(IIa)}$$

$$R^8\text{---}(NR^9\text{---}(CR^{13}R^{14})_n\text{---})_m NR^{10}R^{11}, \quad \text{(IIb)}$$

$$\overline{\phantom{x}\text{---}(NR^{12}\text{---}(CR^{13}R^{14})_p\text{---})_q\phantom{x}}, \quad \text{(IIc)}$$

in which $R^5$, $R^6$ and $R^7$, independently of each other, are in each case hydrogen, $C_1$–$C_{40}$-alkyl, preferably $C_1$–$C_{20}$-alkyl, $C_3$–$C_8$-cycloalkyl, preferably $C_5$–$C_6$-cycloalkyl or $CY^1Y^2$-aryl, where $Y^1$ and $Y^2$, independently of each other, are $C_1$–$C_4$-alkyl, aryl or hydrogen, and aryl is preferably substituted or unsubstituted phenyl, in particular phenyl, aminophenyl, hydroxyphenyl, tolyl, xylyl, nitrophenyl and halophenyl, $R^8$, $R^9$, $R^{10}$, $R^{11}$ and $R^{12}$, in each case independently of each other, are hydrogen, $C_1$–$C_{20}$-alkyl or $C_3$–$C_8$-cycloalkyl, preferably hydrogen or $C_1$–$C_3$-alkyl, where $R^{12}$ can additionally have the meaning of —$(CR^{13}R^{14})_p$—, $R^{13}$ and $R^{14}$, independently of each other, are hydrogen or methyl, m is an integer from 1 to 5, preferably 1 to 2, n is an integer from 2 to 10, preferably 2 to 3, p is an integer from 1 to 8, preferably 1 to 6, and q is an integer from 1 to 5, preferably 1 to 4.

Bases which are additionally preferred in the sense of the present invention are alkali metal carbonates, alkaline earth metal carbonates, alkali metal hydrogen carbonates, alkali metal hydrogen phosphates, alkaline earth metal hydrogen phosphates, alkali metal alcoholates, alkaline earth metal alcoholates, alkali metal hydroxides or alkaline earth metal hydroxides, where alkali metal is preferably lithium, sodium or potassium, and alkaline earth metal is preferably magnesium or calcium, or a mixture of at least two of the abovementioned bases.

For the purposes of the present invention, the amines which are preferably selected are those whose boiling points are high enough to ensure that they remain at the bottom during a distillation, although this is not absolutely necessary. Low-boiling amines can also be subsequently metered in as required, or continuously, where appropriate.

Examples of the amines of the formula (IIa) which are employed according to the invention are: Diethylamine, triethylamine, ethanolamine, diethanolamine, triethanolamine, n- or iso-propylamine, di-n- or di-iso-propylamine, tri-n- or tri-iso-propylamine, n-, iso- or tert-butylamine, amylamine, hexylamine, cyclohexylamine, dicyclohexylamine, stearylamine, oleylamine, tallow fatty amine, coconut alkylamine, distearylamine, dimethylstearylamine and dimethylbenzylamine.

Examples of the amines of the formula (IIb) which are employed according to the invention are: Ethylenediamine, propylenediamine, diethylenetriamine, dipropylenetramine, triethylenetetramine, tripropylenetetramine, 1,4-diaminobutane, 1,5-diaminopentane and 1,6-diaminohexane.

Examples of the amines of the formula (IIc) which are employed according to the invention are: Pyrrolidine, piperidine, piperazine, hexahydro-s-triazine, hexamethylenetetramine, hexamethylenimine or trimethyleneimine.

A mixture of at least two of the abovementioned amines may also be employed.

Those of the above-described alkali metal compounds and alkaline earth metal compounds which are in particular employed according to the invention are: Sodium hydrogen carbonate, sodium carbonate, potassium carbonate, disodium hydrogen phosphate, dipotassium hydrogen phosphate, calcium hydroxide, sodium hydroxide, potassium hydroxide, sodium ethanolate, potassium ethanolate, sodium methanolate, potassium methanolate, sodium propanolate, or a mixture of these bases.

According to the invention, the bases are employed in quantities of 0.01 to 10% by weight, preferably 0.1 to 2% by weight, based on the aminobenzotrifluoride. Quantities of the said bases above 10% by weight are likewise suitable for stabilizing the aminobenzotrifluorides, but are no longer expedient from the ecological point of view, and for reasons of economy.

Examples of aminobenzotrifluorides of the formula (I) which are of interest are:

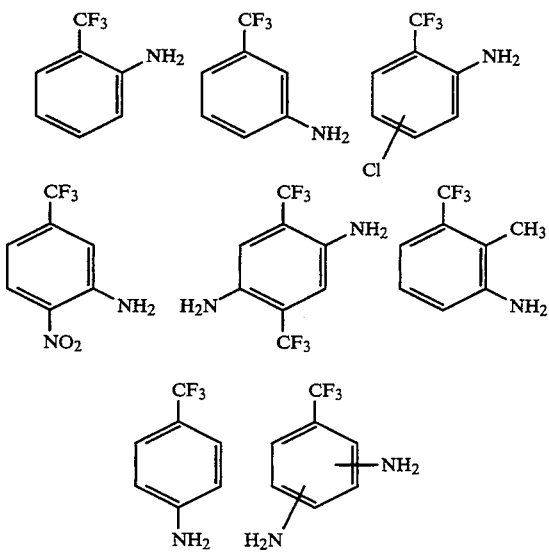

2-Aminobenzotrifluoride, 4-aminobenzotrifluoride and 2-amino-5-chloro-benzotrifluoride are of particular industrial interest.

The present invention furthermore relates to a process for stabilizing aminobenzotrifluorides of the formula (I) defined above, wherein at least one of the above-mentioned bases is added to the aminobenzotrifluoride, preferably before or during a thermal stress, for example a distillation. During a thermal stress, the bases can also be added continuously, or in portions as required. In addition, the bases can be added to the crude or purified aminobenzotrifluoride in order to increase the storage stability.

The stabilizing influence of the said bases on the aminobenzotrifluorides is very high. For example, with the addition of 0.5% by weight of a base, 2-aminobenzotrifluoride can be heated at 150° to 160° C. for several days without decomposition or resinification taking place. No decomposition products can be observed by gas-chromatographic analysis. With the addition of a base, 4-aminobenzotrifluoride remains stable at 150° C. for 5 hours, while without addition it resinifies after only 1.5 hours at 120° C. Amines are particularly suitable for increasing storage stability at more elevated temperatures. The amines dissolve in the aminobenzotrifluorides, so that continuous stirring or circulation of the mixture is unnecessary.

If 2-aminobenzotrifluoride is distilled over the abovementioned bases, the distillate is then more stable than distillates obtained without base addition.

The present invention also relates therefore to the use of the abovementioned bases for increasing the storage stability as well as the thermal stability of aminobenzotrifluorides of the formula (I).

The examples below illustrate the process according to the invention without limiting it thereto.

EXAMPLES

1) Thermal stability of 2-aminobenzotrifluoride (comparative example)

10.0 g (62.1 mmol) of 2-aminobenzotrifluoride were heated at 150° C. under a nitrogen atmosphere. After about 1.5 hours, it was observed that the starting material was becoming yellow and viscous, and after about 2 hours it was completely resinified and solidified. As well as small quantities of starting material, it was possible to detect, by means of GC, GC-MS and MS analyses, about 40% of volatile components with weights greater than 700 g/mol, as well as non-volatile components with high molecular weights, in the resin which had formed.

2) Thermal stability of 4-aminobenzotrifluoride (comparative example)

5.0 g (31 mmol) of 4-aminobenzotrifluoride were heated at 120° C. under a nitrogen atmosphere. After about 1.5 hours, the starting material had completely resinified.

3) Thermal stability of 2-amino-5-chlorobenzotrifluoride (comparative example)

10.0 g (51.2 mmol) of 2-amino-5-chlorobenzotrifluoride were heated at 180° C. under a nitrogen atmosphere. After about 3 hours, the starting material had completely resinified.

The following examples 4 to 21 were carried out with the same result with and without blanketing with nitrogen.

4) Thermal stability of 2-aminobenzotrifluoride following the addition of NaHCO$_3$ 25.0 g (155 mmol) of 2-aminobenzotrifluoride were heated at 150° C. for 56 hours with 0.5 g of NaHCO$_3$ having been added. No resinification was observed. No decomposition products were detectable by means of GC.

5) Thermal stability of 2-amino-5-chlorobenzotrifluoride following the addition of NaHCO$_3$ 25.0 g (128 mmol) of 2-amino-5-chlorobenzotrifluoride were heated at 150° C. for 56 hours with 0.5 g of NaHCO$_3$ having been added. No resinification was observed. No decomposition products were detectable by means of GC.

Examples 6 to 18:

Thermal stability of 2-aminobenzotrifluoride following the addition of various bases The Examples 6 to 18 listed in the following table were carried out in an analogous manner to Example 4 using in each case 100 g (0.62 mol) of 2-aminobenzotrifluoride, and heating at a temperature of 150° C. for 8 hours in each case.

| Example | Base |
|---------|------|
| 6 | 0.5 g of NaHCO$_3$ |
| 7 | 0.5 g of Na$_2$CO$_3$ |
| 8 | 0.5 g of NaOH (solid) |
| 9 | 0.5 g of Na$_2$HPO$_4$ |
| 10 | 0.5 g of Ca(OH)$_2$ |
| 11 | 0.5 g of stearylamine |
| 12 | 0.5 g of dimethylbenzylamine |
| 13 | 0.5 g of triethylamine |
| 14 | 0.5 g of cyclohexylamine |
| 15 | 0.5 g of hexamethylenetetramine |
| 16 | 0.5 g of dimethylstearylamine |
| 17 | 0.5 g of sodium methanolate |
| 18 | 0.5 g of distearylamine |

The 2-aminobenzotrifluoride remained stable in all the listed examples. No resinification or decomposition was observed.

19) Thermal stability of 4-aminobenzotrifluoride following the addition of stearylamine 10.0 g (62.1 mmol) of 4-aminobenzotrifluoride were heated at 150° C. with 0.5 g of stearylamine having been added. The 4-aminobenzotrifluoride remained stable for 5 hours.

20) Thermal stability of 2-amino-5-chlorobenzotrifluoride following the addition of stearylamine 100 g (0.52 mol) of 2-amino-5-chlorobenzotrifluoride were heated at 185° C. with 0.5 g of stearylamine having been added. The 2-amino-5-chlorobenzotrifluoride remained stable for 8 hours. No decomposition or resinification was observed.

21) Thermal stability of 4-aminobenzotrifluoride following the addition of NaHCO$_3$ 10.0 g (62.1 mmol) of 4-aminobenzotrifluoride were heated at 150° C. with 0.5 g of NaHCO$_3$ having been added. The 4-aminobenzotrifluoride remained stable for 5 hours.

22) Distillation of 2-aminobenzotrifluoride with stearylamine having been added 100.0 g (621 mmol) of 2-aminobenzotrifluoride were mixed with 0.5 g of stearylamine and distilled at 80° C./0.04 bar through a 20 cm Vigreux column. The distillate thus obtained is heated at 150° C. Only after 6 hours were there signs of an incipient resinification; after about 7.5 hours the preparation had completely resinified.

We claim:

1. A stabilized aminobenzotrifluoride, composition consisting essentially of
   a) an aminobenzotrifluoride of the formula (I),

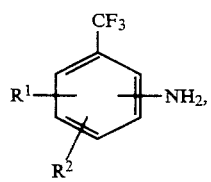

(I)

in which $R^1$ and $R^2$, independently of each other, are hydrogen, $C_1$-$C_6$-alkyl, $C_2$-$C_6$-alkenyl, substituted or unsubstituted aryl, halogen, $CF_3$, nitro, amino, methoxy, hydroxyl or $NR^3R^4$, where $R^3$ and $R^4$ independently of each other, are hydrogen or $C_1$-$C_5$-alkyl radicals, and the $NH_2$ group can be located in the 2-, 3- or 4-position in relation to the $CF_3$ group, and
   b) at least one base.

2. The composition as claimed in claim 1, wherein, in the aminobenzotrifluoride of the formula (I), $R^1$ and $R^2$, independently of each other, are in each case hydrogen, $C_1$-$C_4$-alkyl, $C_2$-$C_4$-alkenyl, fluorine, chlorine, bromine, $CF_3$, $NO_2$, $NH_2$, $OCH_3$, OH, substituted or unsubstituted phenyl, or $NR^3R^4$, in which $R^3$ and $R^4$, independently of each other, are hydrogen or $C_1$-$C_3$-alkyl.

3. The composition as claimed in claim 1, wherein, in the aminobenzotrifluoride of the formula (I), $R^1$ and $R^2$ independently of each other, are in each case hydrogen, methyl, $C_2$-$C_4$-alkenyl, fluorine, chlorine, bromine, $CF_3$, $NO_2$, $NH_2$, $OCH_3$, OH, phenyl, hydroxyphenyl, tolyl, xylyl, aminophenyl, halophenyl, nitrophenyl or $NR^3R^4$, in which $R^3$ and $R^4$, independently of each other, are hydrogen or $C_1$-$C_3$-alkyl.

4. The composition as claimed in claim 1, wherein the aminobenzotrifluoride is 2-aminobenzotrifluoride, 3-aminobenzotrifluoride, 4-aminobenzotrifluoride, 2-amino-5-chlorobenzotrifluoride, 3-amino-4-nitrobenzotrifluoride, 2,5-diamino-4-trifluoromethylbenzotrifluoride, 3-amino-2-methylbenzotrifluoride or a diaminobenzotrifluoride.

5. The composition as claimed in claim 1, wherein the base is a primary, secondary or tertiary amine of the formulae (IIa) or (IIb) or a cycloaliphatic amine of the formula (IIc)

  (IIa)

  (IIb)

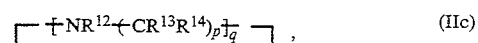  (IIc)

in which
   $R^5$, $R^6$ and $R^7$, independently of each other, are in each case hydrogen, $C_1$-$C_{40}$-alkyl, $C_3$-$C_8$-cycloalkyl, or $CY^1Y^2$-aryl, where $Y^1$ and $Y_2$, independently of each other, are $C_1$-$C_4$-alkyl, aryl or hydrogen, and aryl is substituted or unsubstituted phenyl,
   $R^8$, $R^9$, $R^{10}$, $R^{11}$ and $R^{12}$, in each case independently of each other, are hydrogen, $C_1$-$C_{20}$-alkyl or $C_3$-$C_8$-cycloalkyl, where $R^{12}$ can additionally have the meaning of $-(CR^{13}R^{14})_p-$, $R^{13}$ and $R^{14}$ independently of each other, are hydrogen or methyl,
   m is an integer from 1 to 5,
   n is an integer from 2 to 10,
   p is an integer from 1 to 8, and
   q is an integer from 1 to 5,
or is a mixture of the abovementioned amines.

6. The composition as claimed in claim 1, wherein the base is a primary, secondary or tertiary amine of the formulae (IIa) or (IIb) or a cycloaliphatic amine of the formula (IIc)

  (IIa)

-continued $$R^8\text{-}(NR^9\text{-}(CR^{13}R^{14})_{\overline{n}})_{\overline{m}}NR^{10}R^{11}, \quad \text{(IIb)}$$

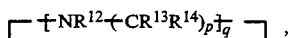 (IIc)

in which
R$^5$, R$^6$ and R$^7$ independently of each other are in each case hydrogen C$_1$–C$_{20}$-alkyl, C$_5$–C$_6$-cycloalkyl or CY$^1$Y$^2$-aryl, where Y$^1$ and Y$^2$, independently of each other, are C$_1$–C$_4$-alkyl, aryl or hydrogen, and aryl is phenyl, aminophenyl, hydroxyphenyl, tolyl, xylyl, nitrophenyl or halophenyl, R$^8$, R$^9$, R$^{10}$, R$^{11}$ and R$^{12}$, in each case independently of each other, are hydrogen or C$_1$–C$_3$-alkyl, where R$^{12}$ can additionally have the meaning of —(CR$^{13}$R$^{14}$)$_p$—, R$^{13}$ and R$^{14}$, independently of each other, are hydrogen or methyl, m is an integer from 1 to 2,
n is an integer from 2 to 3,
p is an integer from 1 to 6, and
q is an integer from 1 to 4,
or is a mixture of the abovementioned amines.

7. The composition as claimed in claim 1, wherein the base is stearylamine, diethylamine, triethylamine, cyclohexylamine, dimethylbenzylamine, ethanolamine, diethanolamine, triethanolamine, n- or iso-propylamine, di-n- or di-iso-propylamine, tri-n- or tri-iso-propylamine, n-, iso- or tert-butylamine, amylamine, hexylamine, cyclohexylamine, oleylamine, tallow fatty amine, coconut alkylamine, distearylamine, dimethylstearylamine, dimethylbenzylamine, ethylenediamine, propylenediamine, diethylenetriamine, dipropylenetriamine, triethylenetetramine, tripropylenetetramine, 1,4-diaminobutane, 1,5-diaminopentane, 1,6diaminohexane, pyrrolidine, piperidine, piperazine, hexahydro-s-triazine, hexamethylenetetramine, hexamethyleneimine, trimethyleneimine, or a mixture of at least two of the said amines.

8. The composition as claimed in claim 1, wherein the base is stearylamine, triethylamine, cyclohexylamine, dimethylstearylamine, distearylamine, hexamethylenetetramine, or a mixture of at least two of the said amines.

9. The composition as claimed in claim 1, wherein the base is an alkali metal carbonate, alkaline earth metal carbonate, alkali metal hydrogen carbonate, alkali metal hydrogen phosphate, alkaline earth metal hydrogen phosphate, alkali metal alcoholate, alkaline earth metal alcoholate, alkali metal hydroxide or alkaline earth metal hydroxide, where alkali metal is lithium, sodium or potassium and alkaline earth metal is magnesium or calcium, or a mixture of the abovementioned bases.

10. The composition as claimed in claim 9, wherein the base is sodium hydrogen carbonate, sodium carbonate, sodium hydroxide, sodium methanolate, disodium hydrogen phosphate, calcium hydroxide, or a mixture of at least two of the said bases.

11. The composition as claimed in claim 1, wherein said composition contains the base in a quantity of 0.01 to 10% by weight, based on the aminobenzotrifluoride.

12. The composition as claimed in claim 1, wherein said composition contains the base in a quantity of 0.1 to 2% by weight, based on the aminobenzotrifluoride.

13. A process for stabilizing aminobenzotrifluorides of the formula (I) as claimed in claim 1, wherein at least one base is added to the aminobenzotrifluoride.

14. The process as claimed in claim 13, wherein the base is added to the aminobenzotrifluoride before or during a thermal stress.

15. A method of increasing the storage stability and the thermal stability of aminobenzotrifluorides of the formula (I)

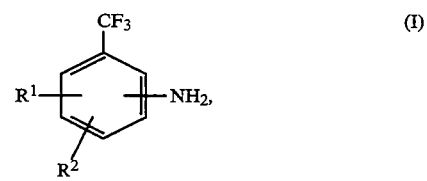

in which
R$^1$ and R$^2$ independently of each other, are hydrogen, C$_1$–C$_6$-alkyl, C$_2$–C$_6$-alkenyl, substituted or unsubstituted aryl, halogen, CF$_3$, nitro, amino, methoxy, hydroxyl, or NR$^3$R$^4$, where R$^3$ and R$^4$, independent of each other are hydrogen or C$_1$–C$_5$-alkyl radicals, and the NH$_2$ group can be located in the 2-, 3-, or 4-position in relation to the CF$_3$ group, comprising the step of adding a base to said aminobenzotrifluoride, said base comprising a primary, secondary, or tertiary amine of the formulae (IIa) or (IIb) or a cycloaliphatic amine of the formula (IIc)

$$R^5R^6R^7N, \quad \text{(IIa)}$$

$$R^8\text{-}(NR^9\text{-}(CR^{13}R^{14})_{\overline{n}})_{\overline{m}}NR^{10}R^{11}, \quad \text{(IIb)}$$

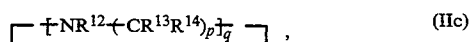 (IIc)

in which
R$^5$, R$^6$, and R$^7$, independently of each other, are in each case hydrogen, C$_1$–C$_{20}$-alkyl, C$_5$–C$_6$-cycloalkyl or CY$^1$Y$^2$-aryl, where Y$^1$ and Y$^2$, independently of each other, are C$_1$–C$_4$-alkyl, aryl, or hydrogen, and aryl is phenyl, aminophenyl, hydroxyphenyl, tolyl, xylyl, nitrophenyl or halophenyl, R$^8$, R$^9$, R$^{10}$, R$^{11}$, R$^{12}$, in each case independently of each other, are hydrogen or C$_1$–C$_3$-alkyl, where R$^{12}$ can additionally have the meaning of —(CR$^{13}$R$^{14}$)$_p$—, R$^{13}$ and $^{14}$, independently of each other, are hydrogen or methyl, m is an integer from 1 to 2,
n is an integer from 2 to 3,
p is an integer from 1 to 6, and
q is an integer from 1 to 4.

* * * * *